United States Patent [19]

Galler

[11] Patent Number: 4,718,852

[45] Date of Patent: Jan. 12, 1988

[54] KIT OF ARMAMENTARIUM FOR RESTORING POSTERIOR TEETH WITH INTERPROXIMAL DECAY

[76] Inventor: Jeffrey M. Galler, 18 Copper Beech La., Lawrence, N.Y. 11516

[21] Appl. No.: 847,286

[22] Filed: Apr. 2, 1986

Related U.S. Application Data

[62] Division of Ser. No. 640,803, Aug. 14, 1984, Pat. No. 4,601,662.

[51] Int. Cl.⁴ ................................................ A61C 7/00
[52] U.S. Cl. ..................................................... 433/148
[58] Field of Search ............................... 433/148, 149

[56] References Cited

U.S. PATENT DOCUMENTS 1,707,952  4/1929  Schneider ........................ 433/144
2,154,751  4/1939  Hoskins .......................... 433/144

FOREIGN PATENT DOCUMENTS

331551  11/1935  Italy ............................. 433/148
726087   3/1965  United Kingdom ................ 433/39

Primary Examiner—Robert Peshock
Attorney, Agent, or Firm—Norbert P. Holler

[57] ABSTRACT

A novel method of restoring posterior teeth such as molars affected by interproximal decay includes drilling the affected tooth, on the side thereof on which the decay is located, essentially horizontally from the buccal to the lingual surface on a line intersecting the site of the decay to form a specially configured groove, scraping the groove clean with a spoon excavator, spreading the two proximate teeth with a separator, inserting a matrix strip between the teeth and anchoring it in place so that it closely overlies the groove, and injecting a dental composite into the groove through an aperture in the matrix. A supply of matrix strips and sets of specially constructed excavators and separators constitute components of a kit of armamentarium for practicing the method. This abstract is not to be taken either as a complete exposition or as a limitation of the present invention, however, the full nature and extent of the invention being discernible only by reference to and from the entire disclosure.

11 Claims, 22 Drawing Figures

KIT OF ARMAMENTARIUM FOR RESTORING POSTERIOR TEETH WITH INTERPROXIMAL DECAY

This application is a division of my prior application Ser. No. 640,803, filed Aug. 14, 1984, now U.S. Pat. No. 4,601,662, issued July 22, 1986.

This invention relates to dental care, and in particular to a novel method of restoring posterior teeth affected by interproximal decay and to a kit of armamentarium usable for that purpose.

Interproximal decay on a posterior tooth such as a premolar is difficult to treat by virtue of its relatively inaccessible location. Heretofore, when a region of decay has been found in the mesial or distal wall of a posterior tooth usually between the gum and the region of contact of the affected tooth with its next adjacent tooth, the dentist has generally utilized a "Class II" preparation technique (so designated in the classification system established by G. V. Black in the early years of the 20th century). Using this technique, it has been conventional practice for the dentist to drill the tooth, in an essentially vertical plane intersecting the site of the decay, so as to form a groove having a generally horizontal section extending partly across the occlusal surface of the tooth and a generally vertical section extending downwardly or upwardly along the side of the tooth past the contact point toward the underlying or overlying gum (depending on whether the affected tooth was a lower tooth or an upper tooth). The so-formed groove, which thus has a generally L-shaped configuration, is then appropriately cleaned out and filled with a dental amalgam. For the filling operation, a flexible metal matrix band is usually wound peripherally around the tooth and tightened thereagainst by means of a suitable tool, such as an "Automatrix" tightener of the type disclosed in U.S. Pat. Nos. 3,435,905 and 3,852,884, to enable that portion of the amalgam which is located in the vertical leg of the groove and replaces the missing interproximal wall of the tooth to be tightly confined therein while it is setting and to provide for the amalgam taking the proper form and contour.

It has long been recognized, however, that this method of restoring a posterior tooth affected by interproximal decay suffers from a number of shortcomings. One of these is that a Class II preparation entails the removal of much sound tooth structure, at the contact point, the marginal ridge and the occlusal surface of the affected tooth (areas frequently completely free of caries) and thus has the potential for unduly and permanently weakening the tooth and making it more susceptible to fracture and to decay at the cavo-surface margins.

For many years, furthermore, dentists have desired to use dental composites rather than amalgams to fill teeth. Dental composite is a plastic material, typically a substance such as bis-GMA or a modification thereof, which is reinforced with an inorganic siliceous filler, typically quartz, fiberglass, silica, or some combination thereof. The plastic resin matrix of such a composite can be polymerized in situ by exposure to ultra-violet light or visible light or by a reaction of benzoyl peroxide and an amine introduced into the matrix from separate containers shortly prior to mixing and placement. Esthetically, dental composites are preferable to amalgams because, since they contain no metal, their color can more closely approximate the color of the tooth being filled and hence be less noticeable. The use of composites in restoring posterior teeth affected by interproximal decay has not come into general vogue, however, because such materials are not able to withstand the stresses and wear to which they are subjected at the contact points and the occlusal surfaces of the teeth. Moreover, when dental composite is used in conjunction with a Class II preparation, which was originally devised for amalgams and not for composites, it is found that contact points are difficult to establish, and voids in the filling are frequently encountered.

It is an important object of the present invention, therefore, to provide a novel method of restoring posterior teeth affected by interproximal decay, which method is not difficult to perform, conserves sound tooth structure at the occlusal surface, the marginal ridge and the contact point of the affected tooth, and lends itself readily to the use of small amounts of dental composites as the filling.

It is also an object of the present invention to provide a kit of specially configured and constructed armamentarium for use in practicing the said method.

Generally speaking, in the practice of the dental restoration method of the present invention, using Bite-wing x-rays as a guide, the tooth affected by the interproximal decay is first drilled with the aid of a suitable bur (e.g. 556 or 557) on either its mesial or its distal surface (depending on whether the region of decay faces the front or the back of the mouth) essentially horizontally from the buccal and lingual sides and at a level between the gum and the contact point of the affected tooth, to form a channel or groove extending continuously from the buccal to the lingual surface of the tooth and intersecting the site of the decay. The groove, viewed longitudinally, thus has a slight curvature corresponding to that of the tooth side where the decay is located. The groove is then cleaned using a suitable bur (e.g. a No. 1, 2 or 3 round bur or a No. 33½, 34 or 35 inverted cone bur) which also serves to extend the gingival floor, the occlusal ceiling and the axial wall or base of the groove. Preferably, during this stage of the preparation, the groove is undercut, i.e. so that its ceiling and floor are non-parallel to each other and diverging from each other inwardly toward the base of the groove. Optionally, the groove may also be dovetailed slightly at its buccal and lingual ends, i.e. formed so that at those regions the base is somewhat enlarged. Either of these configurations will ensure that the filling, when set, will be somewhat wider at the interior of the tooth than at the exterior surface thereof and thus will have increased mechanical rentention in the groove.

It is also contemplated by the present invention, as yet another alternative, that the groove may be so formed that its ceiling and floor are substantially parallel to each other. While this configuration will afford practically no mechanical anchoring for the filling at all, it may be nonetheless acceptable if the acid etch and bonding technique is used to bond the dental composite used as the filling to the relatively narrow portions of the enamel along the boundary of the groove at the tooth surface which are left exposed as a consequence of the drilling operation. In all of the proposed groove configurations, if the bonding technique is utilized, it is recommended that an outwardly slanted or cavo-surface bevel be formed on each of the exposed edges of the enamel at the buccal and lingual end regions of the groove so that, at those locations, a somewhat increased surface area of the exposed enamel is provided to which the filling can bond.

After the groove has been formed, any remaining decay on the occlusal ceiling, gingival floor and axial wall of the groove is scraped out with the aid of a spoon excavator. The excavator may, of course, be either single-ended or double-ended, in the latter case having its two arms on which the respective cutting edges are provided extending in opposite directions relative to the handle of the excavator. For the purposes of the present invention, however, the excavator at each operating end has a special configuration intended to accommodate the difficult accessiblity, the small size, the lack of visibility and the horizontal orientation of the groove in general and of the cavity outline in particular. In a spoon excavator according to the present invention, each arm on which a generally oval or circular cutting edge is formed is oriented at substantially a 90° angle to the excavator handle (in conventional excavators this angle is obtuse, generally about 120° to 135°) while the handle is oriented at an angle of about 30° to a plane which includes the arm and is perpendicular to the general plane of the cutting edge provided thereon. As a minimum, therefore, the kit of armamentarium for the restoration procedure of the present invention will include at least two double-ended excavators constructed in accordance with the present invention, one having its cutting edges oriented for scraping distal caries from the buccal and lingual sides, respectively, and one having its cutting edges oriented for scraping mesial caries from the buccal and lingual sides, respectively. The interior space of a groove will however, depend on the size of the bur used to form it, and it is contemplated that (as already mentioned) three sizes of burs will be used, the choice of any one of them being dictated by the extent of the caries. Thus, it may be desirable to include in the kit three sets of two double-ended excavators having the aforesaid characteristics, each with its spoons or cutting edges sized to fit a respective one of the three sizes of grooves. Alternatively, of course, the kit may include at least four single-ended excavators with respective appropriately oriented cutting edges, and if desired three sets of four such excavators each.

When the groove has been properly scraped out, (if the bonding technique is to be used, pumice and etchant liquid would now be applied in the usual manner) the filling operation is commenced using a new instrument that combines the functions of a separator and a matrix retainer. Initially, the affected tooth and its next adjacent neighbor are spread apart slightly by means of a pair of opposed wedge elements each carried by a respective one of the arms of a dual-armed screw-actuated separator (to this extent the separator is of conventional construction). With the teeth separated, a flexible short matrix strip (made either of metal such as a strip of dead soft metal or, if the dental composite being used is of the light-curing type, of a transparent inert plastic material such as Mylar) is inserted between the teeth so as to overlie the groove and is anchored at at least one end, preferably the lingual end, to the lingual arm of the separator. To perform this function, in accordance with the present invention the constructions of both the separator and the matrix strip are modified somewhat from their conventional form. On the one hand, the separator is provided with means, for example a pair of upstanding pins, for enabling at least one end of the matrix strip to be anchored at either of two spaced locations (depending on whether the filling is to be formed on the mesial or the distal surface of the affected tooth) to at least the lingual one of the separator arms, and on the other hand the matrix strip is correspondingly provided with means, for example a looped or tubular section, at at least one end to facilitate such anchoring. The matrix strip is then tightened over the prepared tooth surface, for example by finger pressure, and preferably is also clamped against the affected tooth with the aid of a wedge, such as a Wizard wedge, inserted from the buccal side. Finally, an injection nozzle or syringe filled with a preferably free-flowing composite is inserted through an aperture in the matrix strip, and the composite is injected into the groove. For this purpose, the matrix strip is preferably provided by the manufacturer with at least one appropriately located aperture for permitting the injection nozzle to be inserted therethrough, but alternatively the strip may initially be entirely imperforate, in which case the dentist will first have to make a suitable puncture in the strip at the buccal side of the tooth to enable him to inject the composite into the groove.

To complete the procedure, after the composite has fully set, the clamping wedge, the matrix strip and the separator are removed from the patient's mouth. One of the advantages of the present invention is that the surface of the filling will be already highly polished and smooth by virtue of the use of the matrix strip, so that additional polishing is not needed. Buccal or lingual excess, if any, is polished away with a fluted bur. If the presence of gingival excess is suspected, of course, that is polished away with thin, successively finer sandpaper strips before the separator is removed. Finally, depending on cosmetic needs or desiderata, the buccal portion of the composite filling may be roughened, etched, color-modified or glazed.

A particular advantage of the procedure of the present invention, over and above its minimizing of the amount of healthy tooth and enamel that has to be destroyed as an incident to the drilling of the groove, is that after the dental composite filling has set or fully cured and the clamping wedge, the matrix strip and the separator have been removed from the mouth of the patient, the filling will be hardly visible, so that the esthetic drawback of the metallic appearance of an amalgam filling is avoided. Yet another advantage is that the filling, by virtue of its location entirely on the gingival side of the contact point, will not be subjected to any of the wear and other stresses (from biting, tooth grinding, etc.) to which a filling extending past the contact point and over the marginal ridge and onto the occlusal surface of the filled tooth is unavoidably subjected.

The foregoing and other objects, characteristics and advantages of the present invention will be more clearly understood from the following detailed description thereof when read in conjunction with the accompanying drawings, in which.

Figure 1:
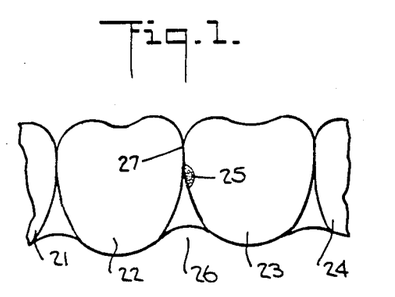
FIG. 1 is a side elevational view of two posterior lower teeth one of which is affected by interproximal decay.
Figure 2:
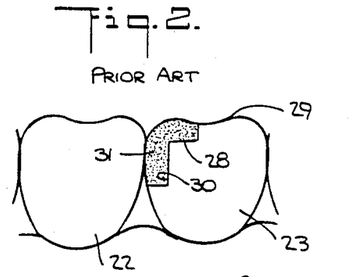
FIG. 2 is a diagrammatic illustration of the heretofore conventional method of removing such interproximal decay from the affected tooth and filling the resultant cavity.

Referring now to the drawings in greater detail, FIG. 1 shows a row of posterior teeth 21, 22, 23 and 24 as viewed from the buccal side thereof at the right side of a patient's mouth, so that of the illustrated teeth the tooth 24 is the one that is closest to the front of the mouth of the patient. The tooth 23 is shown as being affected by interproximal decay 25 on its distal side at a level intermediate the gum line 26 and the contact point 27 between the affected tooth 23 and its confronting next adjacent tooth 22. It will be apparent, therefore, that irrespective of how far towards the rear of the mouth the affected tooth is located, it is a difficult procedure for the dentist to eliminate the decay and restore the tooth. The conventional practice for the dentist when faced with such a case of interproximal decay is to drill the affected tooth essentially in a vertical plane so as to form, as illustrated in FIG. 2, a groove having a generally horizontal leg 28 extending partly across the occlusal surface 29 of the tooth and a generally vertical leg 30 extending downwardly along the side of the affected tooth (or upwardly in the case of an upper tooth) past the site of the decay. The groove is then scraped out with a spoon excavator of conventional construction to remove any traces of the decay, and if desired is flushed out with compressed air and/or water to remove small tooth particles or debris, and it is then filled with a suitable dental amalgam 31 after a flexible metallic matrix strip has been wound about and tightened against the periphery of the tooth to confine the portion of the amalgam 31 in the vertical leg 30 of the groove tightly therein while at the same time the portion of the amalgam in the horizontal leg 28 of the groove is tamped down with an amalgam plugger. The relatively large amount of sound tooth unnecessarily destroyed (considering the small size of the decay) by such a procedure is readily appreciable from FIG. 2.

Figure 3:
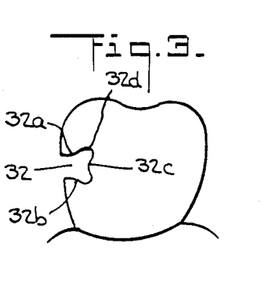
FIG. 3 is a side elevational view of the affected tooth after a preferred form of horizontal groove has been formed therein by the drilling procedure of the present invention.
Figure 3A:
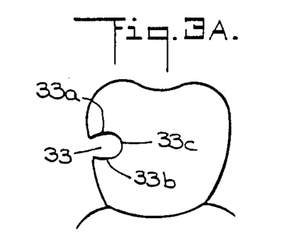
FIGS. 3A and 3B are views similar to FIG. 3 and, respectively, illustrate teeth with grooves of modified configurations drilled into the same.

In contradistinction thereto, in accordance with the procedure of the present invention the aforesaid conventional Class II preparation is completely eliminated and is replaced by a modified drilling approach in which the tooth is drilled essentially horizontally, along a line intersecting the site of the decay 25, in from both the buccal and the lingual sides of the tooth, to form a continuous horizontal groove having, as viewed longitudinally (see FIGS. 8 and 10), a slight convex curvature generally following the contours of the side of the affected tooth where the decay is located. As shown in FIG. 3, in the preferred version of the present invention the groove 32 is primarily formed with an undercut cross-sectional configuration, that is to say, along substantially its entire length the occlusal ceiling 32a and the gingival floor 32b of the groove are non-parallel to and diverge from each other inwardly of the tooth to the base or axial wall 32c of the groove, and it is additionally formed at its buccal and lingual end regions with a somewhat dove-tailed cross-sectional configuration, that is to say, its base is enlarged as shown at 32d. In accordance with the invention, however, the groove just as well can be drilled to have only an undercut cross-sectional configuration, as shown at 33 in FIG. 3A, along its entire length, that is to say, to have only an occlusal ceiling 33a and a gingival floor 33b which diverge from one another inwardly of the tooth toward the base or axial wall 33c of the groove. It will be understood from these illustrations that when a groove of either of these configurations is filled with a dental composite and that composite has fully cured and set, the filling will be solidly mechanically anchored and confined in the groove.

Figure 3B:
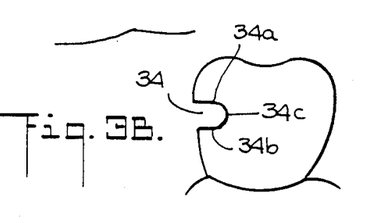

It is also contemplated by the present invention, as an alternative to the aforesaid preferred groove configurations, that the groove may be drilled to have a cross-sectional configuration such as is shown at 34 in FIG. 3B, where the occlusal ceiling 34a and the gingival floor 34b are substantially parallel to one another inwardly of the tooth toward the axial wall or base 34c of the groove. Such a groove configuration, in contrast to those shown in FIGS. 3 and 3A, will afford relatively little if any mechanical anchoring of the filling in the groove. Accordingly, it is contemplated that in conjunction with such a groove the acid etch and bonding technique will be used to ensure the retention of the composite filling in the groove, taking advantage of the fact that the composite will bond well to the exposed portions of the enamel defining the boundary edges of the groove. In all cases where bonding is to be used, it is deemed further advantageous to provide the groove at its buccal and lingual end regions with cavo-surface or outwardly diverging bevels so as to increase somewhat the available surface area of the exposed enamel to which the composite can bond.

It should be noted, in this regard, that the general idea of removing interproximal decay by drilling an affected tooth horizontally, so as to avoid unnecessarily involving the occlusal surface, has been previously discussed in the literature, e.g., as far back as 1897 in the *American Textbook of Operative Dentistry* by Kirk and as recently as 1982 in an article by Roggenkamp et al. entitled "The Facial Slot Preparation: A Nonocclusal Option for Class 2 Carious Lesions" published in the *Journal of Operative Dentistry*, Vol. 7, pages 102–106. Nevertheless, the preparation of teeth by means of such horizontal cutting does not as yet appear to have come into general vogue because until now the instrumentation according to the present invention, described more fully hereinafter, which is required to successfully remove all decay and to successfully fill the cavity with dental composite, has not been available.

Reverting now to the description of the preparation procedure once a groove has been completely drilled, any remaining decay is scraped out with the aid of a spoon excavator having an elongated handle which preferably is double-ended, i.e., it has at its two ends oppositely extending arms each of which is oriented at an angle to the longitudinal axis of the handle and is provided at its outermost extremity with an oval or discoid enlargement or "spoon" having a sharp periphery defining a cutting edge. In a conventional spoon excavator, as previously mentioned, each such arm on which a cutting edge is formed is oriented at an obtuse angle to the axis of the handle, typically between about 120° and 135°, and each cutting edge is arranged so that its general plane substantially coincides with a plane including the axis of the handle. For the purposes of restoring a posterior tooth affected by interproximal decay, however, the location and the small size of the groove drilled in accordance with the present invention make it impractical to use a conventional spoon excavator, because with such a tool the scraping job cannot be done properly by virtue of the fact that the patient's jaw (upper or lower) and adjacent teeth interfere with the positioning and the angular orientation of the excavator handle required to secure the correct orientation of the cutting edge in the groove drilled into the tooth.

Figure 4:
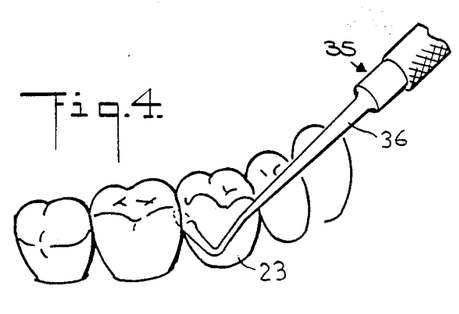
FIG. 4 is a fragmentary elevational view, in perspective, of a row of teeth in one of which a groove of the configuration shown in FIG. 3 drilled into the distal side of the tooth is being scraped out with the aid of a spoon excavator according to the present invention.
Figures 5, 6, 7:
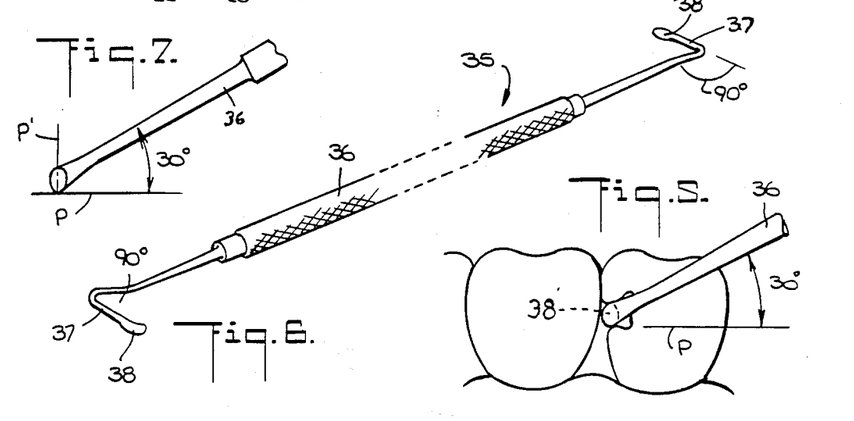
FIG. 5 is a fragmentary side elevational view of the teeth and excavator during the scraping operation illustrated in FIG. 4.
FIG. 6 is an elevational view, in perspective, of a double-ended specially constructed spoon excavator according to the present invention.
FIG. 7 is a fragmentary side elevational view of the excavator shown in FIG. 6.

To avoid this drawback, the present invention contemplates the provision of a modified spoon excavator 35 having, as usual, a handle 36 and, in the double-ended version, a pair of oppositely directed arms 37 on each of which a spoon-shaped cutting edge 38 is formed. In a spoon excavator 35 according to the present invention, however, each of the arms 37 is oriented substantially at a 90° angle to the longitudinal axis of the handle 36 (see FIG. 6), and the handle is oriented at an angle of substantially 30° to a plane P which includes or is parallel to each arm 37 and is perpendicular to the general plane P' of each cutting edge 38 (see FIG. 7). By virtue of this construction, when such a spoon excavator is being used and the cutting edge is disposed, as required, in an essentially vertical plane generally parallel to the axial wall or base of the groove (see FIG. 5), the handle of the excavator is automatically disposed at an angular orientation that enables it to clear the front sections of the upper and lower jaws of the patient and thereby enables the dentist to work without interference by the patient's teeth (see FIG. 4).

It has already been mentioned hereinabove that by virtue of the unique construction of the spoon excavator 35, a dentist's kit of armamentarium for the practice of the preparation procedure according to the present invention should contain as a minimum preferably two double-ended excavators, one with its oppositely directed cutting edges 38 facing toward the handle and being disposed at the appropriate angles for scraping off decay on the distal sides of teeth, and the other with its cutting edges facing away from the handle and being disposed at the appropriate angles for scraping of decay on the mesial sides of teeth. On each excavator, mesial or distal, one end will serve for scraping toward the buccal of lower right and upper left teeth and for scraping toward the lingual of lower left and upper right teeth, while the opposite is true of the other end. Correspondingly, of course, such a kit of armamentarium could include as a minimum a set of four single-ended excavators, two with their cutting edges appropriately oriented for distal scraping and two with their cutting edges appropriately oriented for mesial scraping. However, inasmuch as it is contemplated that (depending on the extent of the decay indicated by the X-rays) any one of three different sizes of burs may be used for drilling a tooth, it would be desirable for the dentist to have available in the kit three sets of either two double-ended or four single-ended spoon excavators, each set characterized by a cutting edge size which is matched to the size of the groove formed by a respective one of the burs.

Figures 8, 9, 10, 11:
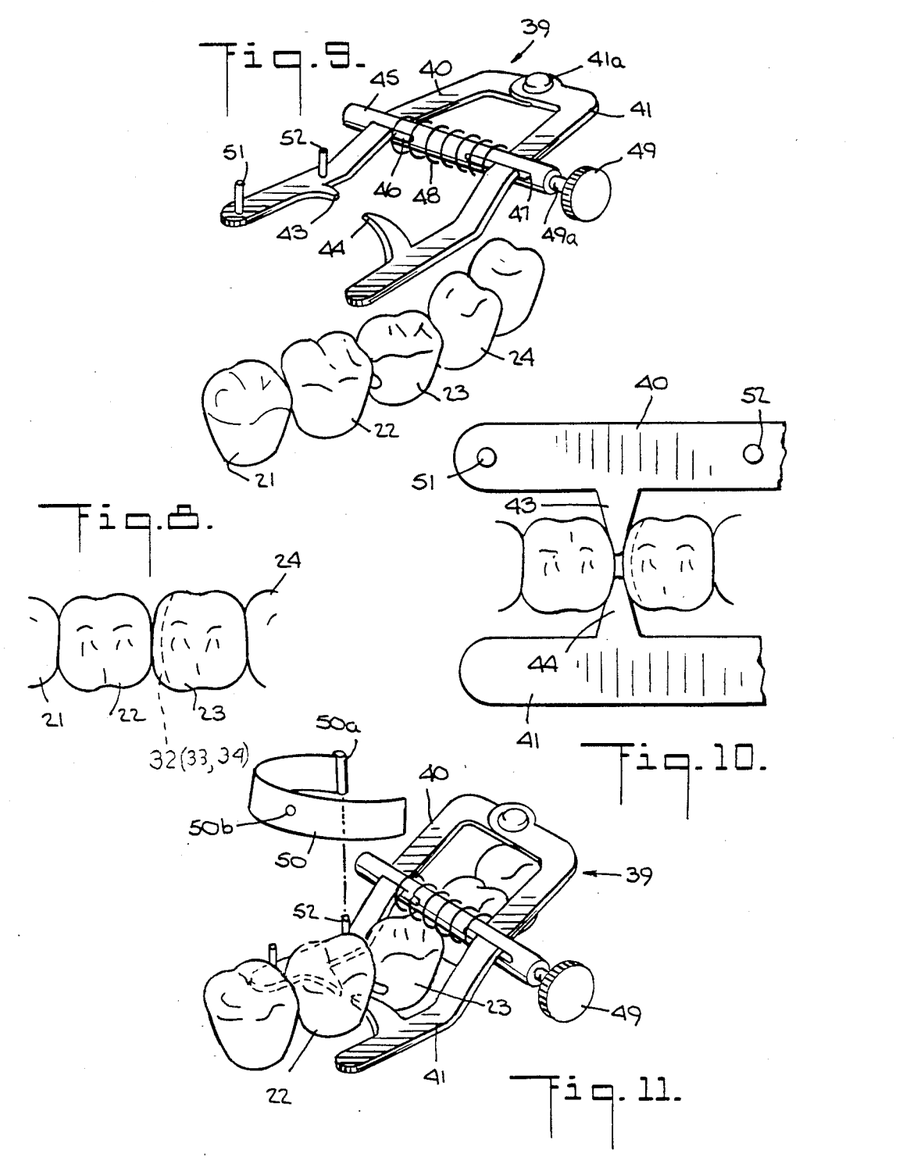
FIG. 8 is a fragmentary plan view of the row of teeth shown in FIGS. 4 and 5 and illustrates the longitudinal outline of the groove drilled into the affected tooth.
FIG. 9 is an elevational view in, perspective, of the said row of teeth as seen looking from the back toward the front of the mouth and illustrates a specially constructed separator according to the present invention prior to its being put into place.
FIG. 10 is a plan view of the teeth similar to FIG. 8 and shows the separator in operative position to spread the affected tooth and its immediate neighbor from one another.
FIG. 11 is a view similar to FIG. 9 but shows the separator in place and the matrix just prior to its insertion between the separated teeth.

After the groove 32, 33 or 34 (FIG. 8) in the affected tooth 23 has been properly prepared, that tooth and its confronting next adjacent tooth 22 are separated slightly from each other by means of a separator 39 (FIGS. 9, 10 and 11). In the illustrated embodiment, the separator 39 includes a pair of arms 40 and 41 hinged or pivoted to each other at one end at 41a and extending away from the pivot connection generally alongside each other at a spacing sufficient to enable one of the arms to be disposed on the lingual side and the other arm to be disposed on the buccal side of the teeth 22, 23 etc. The separator further includes an actuator device 42 for pivoting the arms toward and away from one another, and a pair of mutually opposed wedge-shaped elements 43 and 44 carried by the arms 40 and 41, respectively, and having their apexes disposed in confronting relation to each other, these elements being configured so as to be able to enter into the gingival space between a pair of adjacent teeth and, when pushed thereinto, to force the two teeth apart slightly. For this purpose, the actuator device 42 (see FIG. 9) includes a preferably round rod or bar 45 which extends tranversely to the arms 40 and 41 and has a pair of elongated slots 46 and 47 provided therein intermediate its ends through which the respective arms 40 and 41 extend freely slidably. The actuator device 42 further includes a compression spring 48 surrounding the middle region of the bar or rod 45 and bearing against the inner edges of the arms 40 and 41 so as to bias them apart, and a knob 49 the externally threaded shank 49a of which is screwed into an axial internally threaded bore formed in one end region of the rod or bar 45. The bore extends into communication with the outer end of the slot 47, and the free extremity of the shank 49a projects into the slot 47, there being in engagement with the outer edge of the associated separator arm 41. It will be understood, therefore, that when the knob 49 is, for example, rotated counterclockwise as seen in FIGS. 9 and 11, the innermost end of the threaded shank is retracted outwardly of the slot 47, permitting the spring 48 to displace the arm 41 away from the arm 40 and to increase the spacing between them so as to enable them to bracket the teeth 21 etc. on their lingual and buccal sides. On the other hand, when the knob is rotated clockwise to displace the arm 40 inwardly against the force of the spring, the wedge elements 43 and 44 are brought closer together and caused to enter the desired gingival space (see FIGS. 10 and 11) at a level below that of the groove and ultimately to the degree required to spread the teeth as needed.

To the extent so far described, the separator structure (with the wedge elements 43 and 44 at the free extremities of the arms 40 and 41) is essentially conventional and well known. For the purposes of the present invention, however, the separator structure is modified somewhat and correspondingly so is the structure of the matrix strip 50 (see FIG. 11), because, as previously mentioned, the separator is intended to perform the dual functions of tooth spreading and matrix strip retention and anchoring.

More particularly, the modification of the separator structure is embodied in the fact that the arms 40 and 41 are made longer than usual, so that they extend beyond the locations of the wedge elements 43 and 44, and in the fact that the lingual separator arm 40 is further provided with a pair of rigid, upstanding pins 51 and 52 spaced from each other longitudinally of the arm 40 and disposed one between the wedge element 43 and the extended extremity of the arm and the other between the wedge element 43 an the hinge 41a. At the same time, the matrix strip 50, which may be made of metal or a suitable inert plastic material, is provided at one end with a hollow, generally tubular element or adjunct 50a, the interior size of which is such as to enable it to fit smoothly slidably onto one or the other of the pins 51 and 52. The element 50a, which may be constituted either by a rolled-up portion of the matrix strip itself or by a small tubular element suitably secured to one end of the strip, and the pins 51 and 52 thus constitute cooperative means for anchoring the matrix strip to the separator.

It should be noted, in regard to the use of the separator and the matrix strip, that as a practical matter the separator will always be used with its closed or pivot end directed toward the front of the patient's mouth, with the knob 49 always located at the buccal end of the rod or bar 45, and with the pins 51 and 52 always located on the lingual separator arm 40. The reasons for these choices will be readily apparent to those skilled in the art. The dentist's kit of armamentarium, therefore, preferably should contain a set of two separators 39.

One of these would be constructed as shown in FIGS. 9 and 11, with the lingual arm 40 on the left (as viewed from the open end of the separator) and the buccal arm on the right, and this separator would be used for spreading teeth in the lower right side of the patient's mouth (as in FIGS. 9 and 11) and in the upper left side of the patient's mouth (not shown). The other separator (not shown) would be constructed so as to have its lingual arm on the right and its buccal arm on the left and would be used for spreading teeth in the upper right and lower left sides of the patient's mouth.

Figures 12, 13, 14, 15:
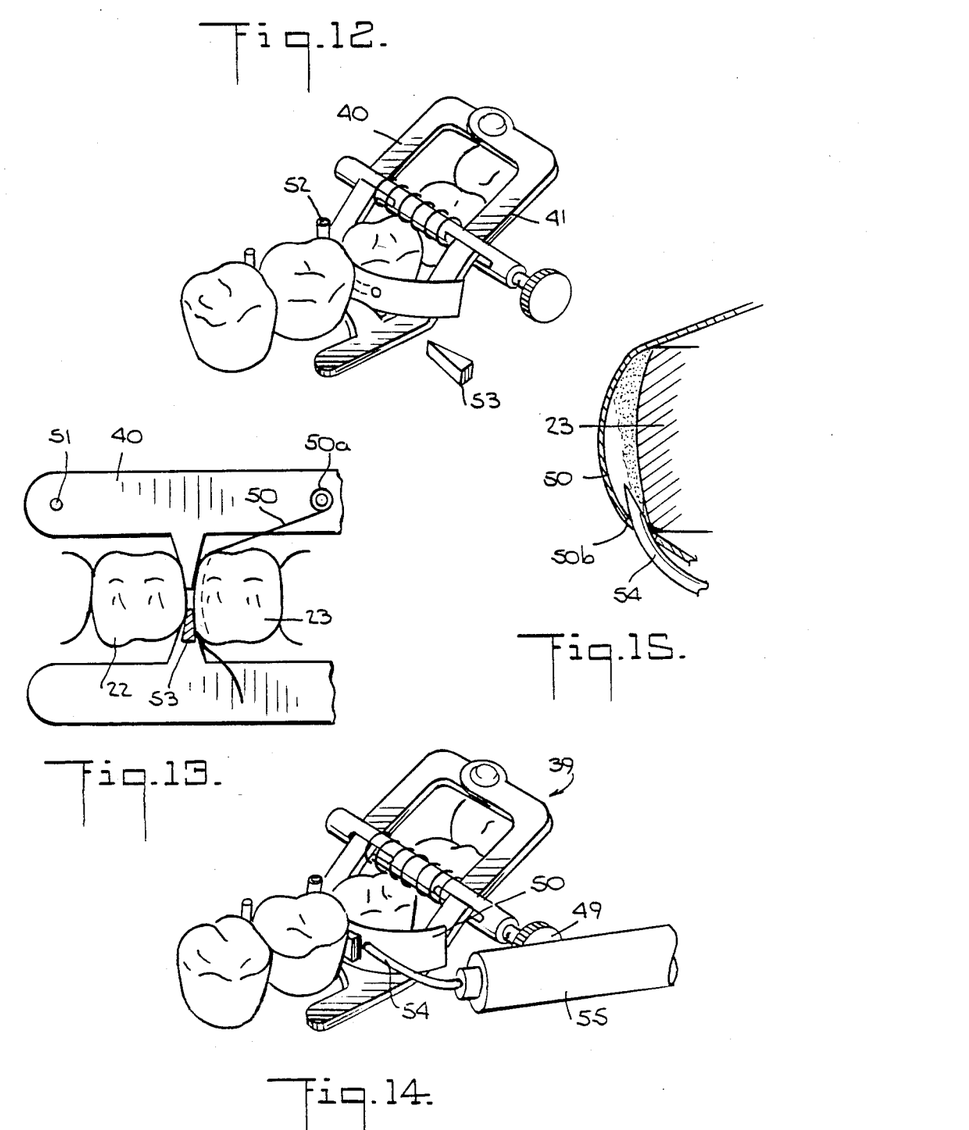
FIG. 12 is a view similar to FIG. 11 but shows the matrix in place and a clamping wedge prior to its insertion between the separated teeth.
FIG. 13 is a plan view similar to FIG. 10 but shows the matrix and the clamping wedge in place.
FIG. 14 is a view similar to FIG. 12 but with the separator, the matrix and the clamping wedge all in place and illustrates the injection of dental composite into the groove through an aperture in the matrix strip.
FIG. 15 is an enlarged fragmentary horizontal section through the drilled tooth and illustrates the injection nozzle extending into the groove within the confines of the matrix.

Reverting now to the procedure in progress, when the teeth 22 and 23 have been sufficiently separated, the matrix strip 50 is inserted between them and its tubular end element or adjunct 50a is fitted onto the anterior pin 52 on the lingual separator arm 40 (see FIGS. 12, 13 and 14). If the bonding technique is to be utilized, the enamel would be prepared in the usual manner prior to placement of the matrix strip. The free end of the matrix strip is then manipulated to tighten the strip against the grooved face of the affected tooth, and a clamping wedge 53 is inserted into the gingival space between the teeth 22 and 23 to solidly clamp the matrix strip in place against the affected tooth. The dental composite is then injected into the groove by means of a suitable injection nozzle such as the tip 54 of a syringe 55. The injection is effected through the matrix strip which, for this purpose, is provided with an aperture or hole 50b (see FIGS. 11 and 15). Preferably, therefore, the dentist's kit of armamentarium should contain a supply of such strips (possibly of different sizes to accomodate different tooth sizes) each of which as furnished by the manufacturer has a hole or aperture 50b pre-formed therein at a spacing from the tubular end element 50a of the strip sufficient to render the hole accessible from the buccal side of the patient's mouth when the strip is in place and to locate it so as to provide access therethrough to the groove drilled into the affected tooth. It is also contemplated by the present invention, however, that the supply of matrix strips may be entirely imperforate, with the dentist puncturing each strip as needed to form the requisite hole therein for the injection operation. It should be noted, in this regard, that the presence of the clamping wedge 53 serves not only to ensure that the matrix strip 50 is held tightly in place but also to minimize the likelihood of the formation of gingival excess, i.e., the overflowing of injected composite out of the groove and into the gingival space between the affected tooth and its next adjacent confronting tooth.

Once the groove has been completely filled, the injected composite is permitted to cure in situ, either by means of a chemical reaction between its reactive components or by means of an irradiation of the injected composite by ultra-violet or visible light; in the latter case, of course, the matrix strip must be transparent or sufficiently translucent to permit such light to pass therethrough and thus will normally be made of a plastic material. When, after a suitable time interval, it is deemed that the composite has been fully cured, the clamping wedge 53 and the matrix strip 50 are removed from the patient's mouth and, if necessary, the procedure is completed, as already described hereinbefore, by polishing away any buccal or lingual excess with the aid of a fluted bur and by polishing away any gingival excess with the aid of sandpaper strips while the separator 39 is still in place. After the finishing operations have been completed, the separator is removed.

The present invention further contemplates a number of variants of the procedure and equipment so far described herein.

Figure 16:
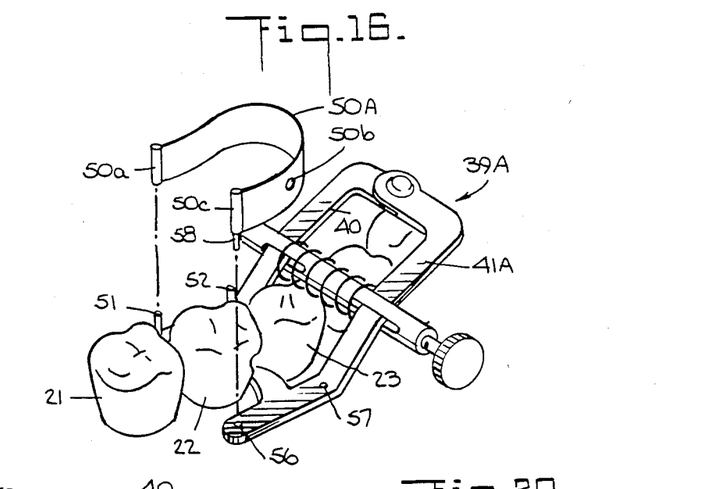
FIG. 16 is a view similar to FIG. 11 but illustrates somewhat modified forms of the separator and the associated matrix strip and shows the groove as formed on the mesial side of an affected tooth.
Figures 17, 18, 19, 20:
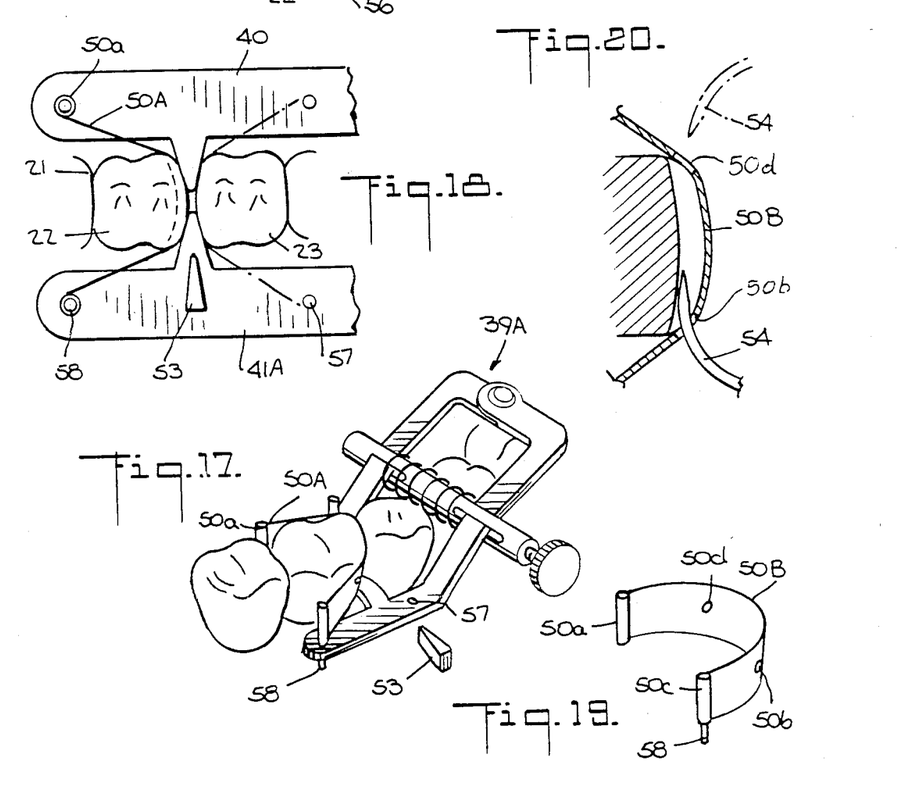
FIG. 17 is a view similar to FIG. 16 but shows the modified matrix in place between the separated teeth and anchored at both ends to the respective arms of the separator and shows a clamping wedge prior to its insertion between the separated teeth.
FIG. 18 is a fragmentary plan view of the teeth and equipment shown in FIG. 17.
FIG. 19 is a perspective illustration of a matrix strip provided with dual apertures according to a modification of the present invention.
FIG. 20 is an enlarged fragmentary horizontal section through a drilled tooth as shown in FIG. 17 and with the groove overlaid by a dual-apertured matrix strip as shown in FIG. 19.

For example, in FIGS. 16, 17 and 18 there are shown a modified separator 39A and a modified matrix strip 50A (here shown as being used in a restoration on the mesial side of the tooth 22) which are designed for enabling the matrix strip to be anchored at both ends to the respective separator arms. Accordingly, whereas the lingual separator arm 40 is unchanged from its form in the principal embodiment, the buccal separator arm 41A is provided with at least one pair of holes 56 and 57 generally corresponding in location to the pins 51 and 52 on the lingual separator arm 40, and correspondingly the matrix strip is provided at its second end 50c with a protruding pin 58 suitably secured thereto and adapted to be received in either of the holes 56 and 57 (more than one hole 56 and one hole 57 may, of course, be provided to enable the second anchoring location to be adjusted so as to accommodate teeth of different sizes). Even in a dual anchor arrangement, however, it is preferred for a Wizard clamping wedge 53 to be used (FIGS. 17 and 18) to retain the advantage of minimizing gingival excess.

As yet another possible variant of the invention there is shown in FIGS. 19 and 20 a matrix strip 50B which differs from the strip 50A only in that it is provided with a second hole or aperture 50d. It will be understood, of course, that such a second hole could also be provided in the matrix strip 50 shown in FIG. 11. As can be seen from the solid-line and broken-line illustrations in FIG. 20, when a matrix strip is provided with two holes or apertures 50b and 50d it is possible to use either one as the opening for accommodating the nozzle 54 during the actual injection operation. The other hole will then afford a visual indication of when the groove drilled into the affected tooth has been filled, which can be judged from the fact that some of the injected dental composite will be seen emerging via the second hole.

It will be understood that the foregoing description of preferred embodiments of the present invention is for purposes of illustration only, and that the various structural and operational features herein disclosed are susceptible to a number of modifications and changes none of which entails any departure from the spirit and scope of the present invention as defined in the hereto appended claims. For example, many dentists may wish to put on the separator before drilling so as to have better access and visibility and to minimize trauma to the adjacent tooth and gingiva. It might also be feasible for one separator/matrix holder to replace the two referred to earlier and to be used in all quadrants of the patient's mouth, by constructing it with anchoring pins on both arms and by providing the actuator device with threaded bores at each end of the rod or bar 45 so as to enable the latter to receive the knob 49 at either end.

What is claimed is:

1. A dental separator for spreading apart from each other at their contact point two posterior teeth at least one of which is affected by interproximal decay, comprising a pair of elongated arms pivotally connected to each other and having respective sections extending away from the pivot connection generally alongside each other at a spacing sufficient to enable one of said sections to be disposed on the lingual side and the other of said sections to be disposed on the buccal side of the teeth to be spread apart, each of said arms carrying in said section thereof intermediate the pivot connection and the free extremity of said section a respective wedge element having an apex, each of said wedge elements extending from its associated arm toward the other arm and having its apex in confronting relation to the apex of the other wedge element, both said wedge elements being shaped and dimensioned to be able to enter into the gingival space between the teeth to be spread apart, actuator means interconnected with said arms for selectively displacing said sections thereof toward and away from each other for forcing said wedge elements into and retracting them from said gingival space, and respective first means carried by said section of said one arm, one between the associated wedge element and the pivot connection and one between the associated wedge element and the free extremity of said section of said one arm, for enabling one end of a matrix strip to be anchored to said one arm.

2. A dental separator as claimed in claim 1, wherein said respective first means comprise two upstanding pins on said section of said one arm for receiving a tubular end element of a matrix strip.

3. A dental separator as claimed in claim 1, wherein said section of said other arm is provided with respective second means, at locations corresponding to those of said first means on said section of said one arm, for enabling a second end of a matrix strip to be anchored to said other arm.

4. A dental separator as claimed in claim 3, wherein said respective second means comprise at least one pair of holes for receiving a pin end element of a matrix strip.

5. Equipment for use in a dental restoration procedure on a posterior tooth affected by interproximal decay, said equipment comprising in combination:

(a) a dental separator for spreading apart from each other at their contact point two posterior teeth at least one of which is affected by said interproximal decay, said dental separator comprising a pair of elongated arms pivotally connected to each other and having respective sections extending away from the pivot connection generally alongside each other at a spacing sufficient to enable one of said sections to be disposed on the lingual side and the other of said sections to be disposed on the buccal side of the teeth to be spread apart, each of said arms carrying in said section thereof intermediate the pivot connection and the free extremity of said section a respective wedge element having an apex, each of said wedge elements extending from its associated arm toward the other arm and having its apex in confronting relation to the apex of the other wedge element, both said wedge elements being shaped and dimensioned to be able to enter into the gingival space between the teeth to be spread apart, actuator means interconnected with said arms for selectively displacing said sections thereof toward and away from each other for forcing said wedge elements into and retracting them from said gingival space, and respective first means carried by said section of said one arm, one between the associated wedge element and the pivot connection and one between the associated wedge element and the free extremity of said section of said one arm, for enabling one end of a matrix strip to be anchored to said one arm; and (b) a matrix strip adapted to be wrapped, after removal of the interproximal decay, over the surface of the affected posterior tooth where the interproximal decay was located, said strip having at one end thereof a first element adapted to be interengaged with and thereby anchored to either of said respective first means on said one arm of said dental separator.

6. Equipment as claimed in claim 5, wherein said respective first means on said dental separator comprise two upstanding pins on said section of said one arm of said dental separator, and said first element of said matrix strip is a tubular structure adapted to be fitted over either of said upstanding pins.

7. Equipment as claimed in claim 5, wherein said section of said other arm of said dental separator is provided with respective second means, at locations corresponding to those of said first means on said section of said one arm, for enabling a second end of a matrix strip to be anchored to said other arm, and said matrix strip at its other end has a second element adapted to be interengaged with and thereby anchored to either of said respective second means on said other arm of said dental separator.

8. Equipment as claimed in claim 7, wherein said respective second means on said dental separator comprise at least one pair of holes in said section of said other arm of said dental separator, and said second element of said matrix strip is a pin structure adapted to be received in any of said holes in said other separator arm.

9. Equipment as claimed in claim 8, wherein said respective first means on said dental separator comprise two upstanding pins on said section of said one arm of said dental separator, and said first element of said matrix strip is a tubular structure adapted to be fitted over either of said upstanding pins.

10. Equipment as claimed in claim 5, wherein said matrix strip further has intermediate its ends a hole positioned so that, when said matrix strip overlies a generally horizontal groove drilled into the affected tooth at the location of said interproximal decay, said hole communicates with the groove and enables the injection of a dental composite into the groove through said hole.

11. Equipment as claimed in claim 5, wherein said matrix strip further has intermediate its ends a pair of holes positioned so that, when said strip overlies a generally horizontal groove drilled into the affected tooth at the location of said interproximal decay, each of said holes communicates with the groove, one at the lingual and one at the buccal end region thereof, and enables the injection of a dental composite into the groove through either of said holes and the exiting of injected composite through the other hole to provide visual indication of the groove being completely filled.

* * * * *